US012661369B2

(12) United States Patent
Nakagawara et al.

(10) Patent No.: US 12,661,369 B2
(45) Date of Patent: *Jun. 23, 2026

(54) MUSCULAR ATROPHY INHIBITOR AND METHOD FOR INHIBITING MUSCULAR ATROPHY

(71) Applicant: YAMASA CORPORATION, Choshi (JP)

(72) Inventors: Kosuke Nakagawara, Choshi (JP); Chieri Takeuchi, Choshi (JP); Kazuya Ishige, Choshi (JP)

(73) Assignee: YAMASA CORPORATION, Choshi (JP)

(*) Notice: Subject to any disclaimer, the term of this patent is extended or adjusted under 35 U.S.C. 154(b) by 441 days.

This patent is subject to a terminal disclaimer.

(21) Appl. No.: 18/258,977

(22) PCT Filed: Dec. 27, 2021

(86) PCT No.: PCT/JP2021/048703
§ 371 (c)(1),
(2) Date: Jun. 22, 2023

(87) PCT Pub. No.: WO2022/145439
PCT Pub. Date: Jul. 7, 2022

(65) Prior Publication Data
US 2024/0041910 A1 Feb. 8, 2024

(30) Foreign Application Priority Data

Dec. 28, 2020 (JP) ................................. 2020-218130

(51) Int. Cl.
*A61K 31/7072* (2006.01)
*A61K 31/7068* (2006.01)
*A61P 21/00* (2006.01)

(52) U.S. Cl.
CPC ...... *A61K 31/7072* (2013.01); *A61K 31/7068* (2013.01); *A61P 21/00* (2018.01)

(58) Field of Classification Search
None
See application file for complete search history.

(56) References Cited

U.S. PATENT DOCUMENTS 7,915,233 B1 3/2011 Von Borstel

FOREIGN PATENT DOCUMENTS

| | | |
|---|---|---|
| JP | 10203989 A | 8/1998 |
| JP | 2010248161 A | 11/2010 |
| JP | 2016160183 A | 9/2016 |
| JP | 2017061466 A | 3/2017 |
| JP | 2018105550 A | 7/2018 |
| JP | 2018521993 A | 8/2018 |
| WO | WO-0011952 A1 * 3/2000 ............. A61P 43/00 |
| WO | 2012091549 A1 7/2012 |
| WO | 2016205671 A1 12/2016 |

OTHER PUBLICATIONS

Written Opinion of the ISR issued in PCT/JP2021/048703, dated Jul. 4, 2023.
Kuznetsova et al.; Effect of potassium orotate and sodium uridine monophosphate on the development of experimental adrenaline myocardiodystrophy. Farmakologiya i Toksikologiya, 1981, vol. 44, No. 2, pp. 170-173, ISSN 0014-8318.
Engel, W. K.; Uridine as a Possible Treatment for Amyotrophic Lateral Sclerosis (ALS): Hypothesis and Phase-I-Study Demonstrating Safety. Neurology, 1988, vol. 38, No. 3. supplement 1, pp. 326, abstract No. PP537.
Wang. D. et al.; Baoyuan Jiedu Decoction Alleviates Cancer-Induced Myotube Atrophy by Regulating Mitochondrial Dynamics Through p38 MAPK/PGC-lalpha Signaling Pathway; Frontiers in Oncolog, Sep. 30, 2020, vol. 10, article 523577, ISSN 2234-943X.
ISR issued in PCT/JP2021/048703, mailed Mar. 1, 2022.
EESR issued in corresponding European patent application No. 21915297.2, dated Oct. 28, 2024.

* cited by examiner

*Primary Examiner* — Patrick T Lewis
(74) *Attorney, Agent, or Firm* — Gregory P. Einhorn; Greer, Burns & Crain, Ltd.

(57) ABSTRACT

The present invention is a muscular atrophy inhibitor comprising at least one pyrimidine nucleotide or a precursor thereof as an active ingredient. Also, the present invention is a method for inhibiting muscular atrophy by administrating at least one pyrimidine nucleotide or a precursor thereof.

21 Claims, 7 Drawing Sheets

MUSCULAR ATROPHY INHIBITOR AND METHOD FOR INHIBITING MUSCULAR ATROPHY

TECHNICAL FIELD

The present invention relates to a muscular atrophy inhibitor and a method for inhibiting muscular atrophy.

BACKGROUND ART

Skeletal muscle is the largest organ accounting for approximately 40% of the body weight of adults. Skeletal muscle plays an important role not only in exercise and postural maintenance, but also in maintenance of body temperature through heat production and in regulation of blood glucose levels as a target organ for insulin.

Reduction of physical functions due to atrophy of skeletal muscle causes falls, fractures, and other problems. This leads to a vicious cycle of further reduction of physical functions and muscular atrophy, which ultimately causes defects in daily activities and deteriorates the quality of life (QOL). Therefore, a countermeasure against muscular atrophy is an important issue for maintaining and improving QOL.

The exercise is an effective means for quantitatively and qualitatively increasing skeletal muscle mass, but elderly persons and the like are often difficult to perform continuous exercise at a sufficient intensity. For this reason, nutritional approaches have been studied to improve skeletal muscle functions.

Skeletal muscular atrophy is caused by a variety of factors and is classified into several types depending on the causes of symptoms and like. The Skeletal muscle is known to atrophy with ageing, and such age-related muscular atrophy is called sarcopenia (age-related muscle weakness). In addition to aging, it is also known that skeletal muscle atrophies due to prolonged disuse of muscle by being bedridden, excessive resting conditions, weightless environments, or the like, which is called disuse muscular atrophy.

Recently, it has revealed that muscular atrophy involves the enhancement of a ubiquitin-proteasome proteolytic system. Atrogin-1 and MuRF1 are ubiquitin-proteasome proteolytic genes which are upregulated during various types of muscular atrophy including age-related loss of muscle mass, and play important roles in muscular atrophy (Non-Patent Literature 1).

It has also revealed that glucocorticoids are involved in the enhancement of the ubiquitin-proteasome proteolytic system. Dexamethasone, a synthetic glucocorticoid, binds to glucocorticoid receptors in a muscle tissue and then increases the expression of Atrogin-1 and/or MuRF1 which is/are the ubiquitin-proteasome system, thereby inducing protein degradation and evoking muscular atrophy. The dexamethasone-induced metabolic change is similar to muscular atrophy in animal or human, and the dexamethasone-induced muscle atrophy model is commonly used in muscular atrophy research (Non-Patent Literature 2). Therefore, materials that inhibit the expression of the ubiquitin-proteasome system, such as Atrogin-1, in the dexamethasone-induced muscle atrophy model, may be effective to suppress the muscular atrophy.

Recently, muscular atrophy inhibitors using food materials and the like have been reported. For example, Patent Literature 1 discloses a peptide that exhibits a ubiquitin ligase inhibitory activity in vitro. Also, Patent Literature 2 discloses a peptide that exhibits an effect of suppressing myotube atrophy induced by treating myotube cells derived from a mouse skeletal muscle cell line (C2C12) with dexamethasone, and an effect of suppressing Atrogin-1 expression in dexamethasone-administered model mice.

Cytidylic acid and uridylic acid are a kind of nucleotides, and are substances widely contained in or added to living organisms and foods, and are extremely safe and ideal materials for addition to foods. Patent Literature 3 describes an agent for improving emotional disorders characterized by containing a nucleotide.

Patent Literature 4 discloses an anti-fatigue agent or physical strength improving agent containing uridine, uracil, uridylic acid, or a uridine derivative, or a pharmaceutically acceptable salt thereof, and it also discloses that the running time limit during treadmill running is prolonged in mice that have orally administered uridine. Also, Non-Patent Literature 2 discloses that rats which have administered a mixture of cytidylic acid and uridylic acid tolerate prolonged treadmill exercise.

However, the improvement of the physical strength described in the above Patent Literature 4 and Non-Patent Literature 2 refers to the improvement of the ability to continuously perform a certain exercise condition, such as on the treadmill, which can be an evaluation of a different phenomenon from the suppression of muscular atrophy associated with aging or disuse of muscle, and the like.

Patent Literature 5 describes a composition containing uridine and/or uridylic acid and various other ingredients for use in preventing or treating weakness in mammals, and it also discloses that one specific example of the prevention or treatment of weakness is an increase in muscle mass.

However, Examples of the Patent Literature 5 only demonstrate that, when a diet containing UMP and DHA was administered to Alzheimer's disease model mice, they had a higher rate of weight gain than mice that fed a control diet, and when a beverage supplemented with UMP, EPA, DHA, lecithin, choline, vitamin E, vitamin C, selenium, and B-vitamins were administered to elderly human patients suffering from cognitive disorders, the BMI value was increased as compared to patients receiving a control beverage, and the ADL (ADCS score) was improved especially in patients having BMI of less than 26.

In other words, although the patent Literature 5 mentions the muscle mass as one of the various symptoms of "weakness", it only evaluates the weight gain in both mouse and human studies, and it does not directly measure the muscle mass or examine the relevant gene expression at all. In addition, the patent Literature 5 only performs Examples that simulates the Alzheimer's disease, and it does not examine the effect of suppressing the entire muscular atrophy.

Also, the beverages administered to elderly patients contain various ingredients other than UMP, and it is not understood from the studies that UMP itself has an effect of improving weight loss. ADL is considered to be the ability to independently perform activities of daily living such as bathing, dressing, and moving, which cannot be an index that focuses on muscle strength at all.

Therefore, whether nucleotides such as cytidylic acid and uridylic acid or nucleosides such as cytidine and uridine actually have an effect of inhibiting muscular atrophy has not been conventionally examined and has not been revealed at all.

CITATION LIST

Patent Literatures

[PTL 1]
Japanese Patent Application Publication No. 2016-160183 A
[PTL 2]
Japanese Patent Application Publication No. 2018-105550 A
[PTL3]
Japanese Patent Application Publication No. H10-203989 A
[PTL 4]
Japanese Patent Application Publication No. 2010-248161 A
[PTL 5]
Japanese Patent Application Publication No. 2017-061466 A Non-Patent Literatures

[NON-PTL 1]
Stewart H. Lecker, et al., "Multiple types of skeletal muscle atrophy involve a common program of changes in gene expression", FASEB J. 18: 39-51, 2004
[NON-PTL 2]
Michael Menconi, et al., "Dexamethasone and corticosterone include similar, but not identical, muscle wasting responses in cultured L6 and C2C12 myotubes", J Cell. Biochem., 105, 353-364, 2008

SUMMARY OF INVENTION

Problem to be Solved by the Invention

An object of the present invention is to provide a novel and highly safe muscular atrophy inhibitor that exhibits a muscle atrophy inhibiting effect when it is used as a food, feed, drug, quasi-drug, or the like.

Methods for Solving the Problem

As a result of intensive studies to achieve the above object, the present inventors have first found that pyrimidine nucleotides or precursors thereof have a clear effect of inhibiting muscular atrophy, in addition to the effect of improving physical strength which is conventionally known in the art, and they have completed the present invention.

In other words, the present invention is a muscular atrophy inhibitor comprising at least one pyrimidine nucleotide or a precursor thereof as an active ingredient.

Also, the present invention is a method for inhibiting muscular atrophy, wherein the method comprises administrating at least one pyrimidine nucleotide or a precursor thereof.

Effects of Invention

The muscular atrophy inhibitor comprising at least one pyrimidine nucleotide or a precursor thereof as an active ingredient according the present invention will provide a novel means for improving the quality of life of patients and elderly persons suffering from muscular atrophy. Further, by using the muscle atrophy inhibitor according to the present invention before the onset of muscle atrophy, its prevention is also possible.

DETAILED DESCRIPTION OF THE INVENTION

Figure 1:
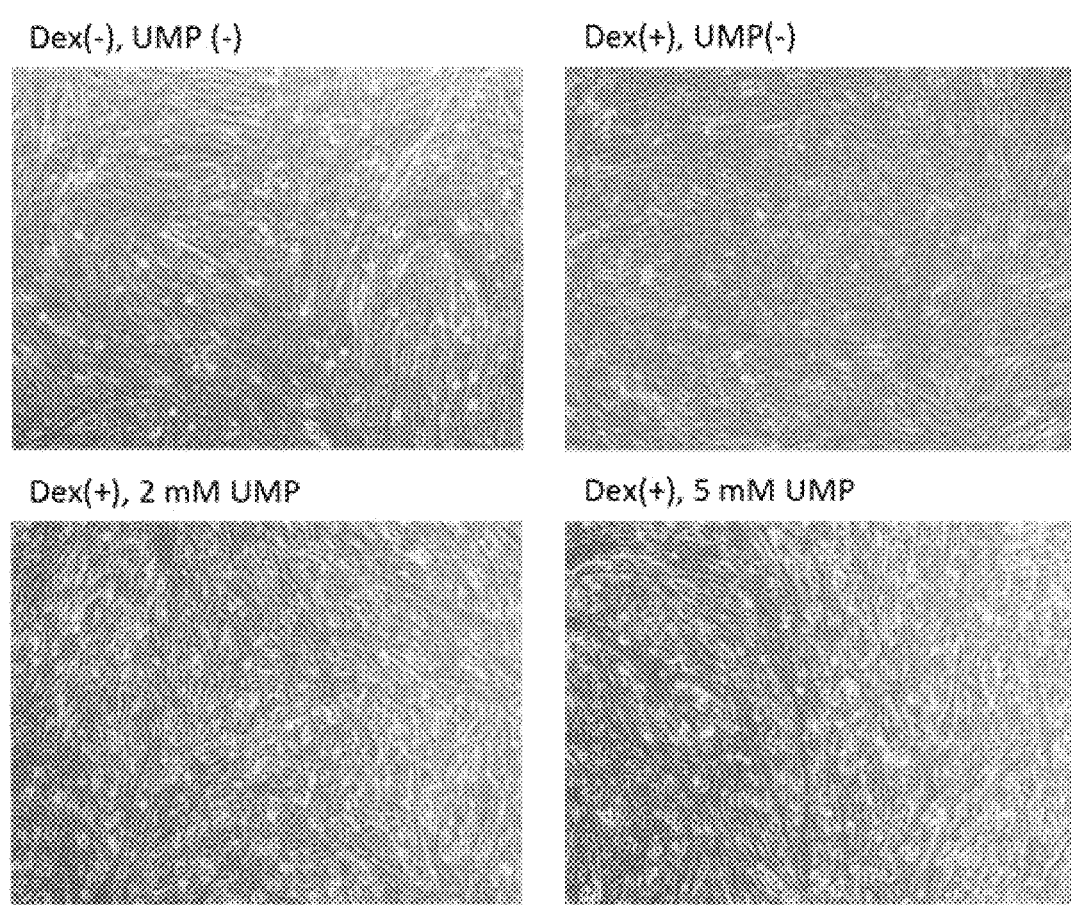
FIG. 1 shows an effect of uridylic acid on inhibition of dexamethasone-induced muscular atrophy in C2C12 cells according Example 1-1 by photographs at magnifications of 100. In the figure, the Dex means dexamethasone and the UMP means disodium uridylate.

The present invention relates to a muscular atrophy inhibitor containing at least one pyrimidine nucleotide or a precursor thereof as an active ingredient.

As used herein, the muscular atrophy refers to reduction of muscle and loss of muscle mass due to decomposition of skeletal muscle making up the muscle.

As used herein, the inhibition of muscle atrophy refers to suppressing, delaying, reversing or preventing the progression of the muscle atrophy.

Also, as used herein, the inhibition of muscle atrophy may also mean inhibition of the expression of genes relating to the ubiquitin-proteasome proteolytic system, and may also mean inhibition of the expression of the Atrogin-1 gene as a gene relating to the ubiquitin-proteasome proteolytic system. It is known, for example, from Non-Patent Literatures 1 and 2, that the inhibited expression of the genes relating to the ubiquitin-proteasome proteolytic system is involved in the inhibition of muscular atrophy.

The muscular atrophy inhibitor according to the present invention contains at least one pyrimidine nucleotide or a precursor thereof as an active ingredient. The pyrimidine nucleotide or the precursor thereof is suitable as an active ingredient according to the present invention in terms of safety as food or the like, and ease of absorption into the body.

As used herein, the pyrimidine nucleotide means cytidylic acid and uridylic acid.

The cytidylic acid (cytidine monophosphate, cytidine 5'-phosphate, CMP) is a compound represented by CAS Registry Number 63-37-6. When cytidylic acid is mentioned herein, salts of cytidylic acid are also included.

When a mass of cytidylic acid is described herein, it represents a mass when converted to disodium cytidylate (CMP,2Na). When a concentration (%) of cytidylic acid is mentioned herein, it is a mass volume percent concentration (w/v %) unless otherwise specified, and a mass converted to CMP,2Na is used as the mass of cytidylic acid. If a salt other than the disodium salt is selected, or if it is a free acid that does not form a salt, it is a mass when converted to CMP,2Na, based on the substance material of the cytidylic acid.

Uridylic acid (uridine monophosphate, uridine 5'-phosphate, UMP) is a compound represented by CAS registration number 58-97-9. When the term "uridylic acid" is used herein, it is concept also including salts of uridylic acid.

When a mass of uridylic acid is described herein, it represents a mass when converted to disodium uridylate (UMP,2Na). When a concentration (%) of uridylic acid is mentioned herein, it is a mass volume percent concentration (w/v %) unless otherwise specified, and a mass converted to UMP,2Na is used as the mass of uridylic acid. If a salt other than the disodium salt is selected, or if it is a free acid that does not form a salt, it is a mass when converted to UMP,2Na, based on the substance material of the uridylic acid.

As used herein, a pyrimidine nucleotide precursor means a compound that can be metabolized to the pyrimidine nucleotide, i.e., cytidylic acid and/or uridylic acid. Whether a compound is included in the pyrimidine nucleotide precursor is determined by the presence or absence of knowledge that the compound is converted to the pyrimidine nucleotide. Specifically, cytidine diphosphate, cytidine triphosphate, uridine diphosphate, and uridine triphosphate, which are known to be degraded to cytidylic acid and/or uridylic acid by the action of ectonucleotidases and like (Isao Matsuoka, "Ectonucleotidases in Nervous System", Clinical Chemistry 33: 11-18, 2004), and cytidine, cytosine, uridine, and uracil, which are known to be phosphorylated to cytidylic acid and/or uridylic acid by the action of kinases (A Orengo, "Regulation of enzymatic activity by metabolites. I. Uridine-cytidine kinase of Novikoff ascites rat tumor", J Biol Chem. 1969 Apr. 25; 244(8): 2204-9.) are exemplified as pyrimidine nucleotide precursors as used herein.

Examples of the pyrimidine nucleotides or precursors thereof in the present invention include, as described above, cytidine, cytosine, cytidylic acid, cytidine diphosphate, cytidine triphosphate, uridine, uracil, uridylic acid, uridyl diphosphate, and uridyl triphosphate. Among them, cytidylic acid, uridylic acid, cytidine, and uridine are preferred.

The concept of cytidylic acid as used herein includes salts as described above. The salts of cytidylic acid include alkali metal salts such as sodium and potassium salts; alkaline earth metal salts such as calcium, magnesium and barium salts; basic amino acid salts such as arginine and lysine; ammonium salts such as ammonium and tricyclohexylammonium salts; and various alkanolamine salts such as monoethanolamine salts, diethanolamine salts, triethanolamine salts, monoisopropanolamine salts, diisopropanolamine salts and triisopropanolamine salts. Preferably, the salts may be alkali metal salts such as sodium salts. Specific examples of such alkali metal salts include monosodium cytidylate and disodium cytidylate, disodium cytidylate being preferred from the standpoint of handleability.

The concept of uridylic acid as used herein includes salts as described above. The salts of uridylic acid include alkali metal salts such as sodium and potassium salts; alkaline earth metal salts such as calcium, magnesium and barium salts; basic amino acid salts such as arginine and lysine; ammonium salts such as ammonium and tricyclohexylammonium salts; and various alkanolamine salts such as monoethanolamine salts, diethanolamine salts, triethanolamine salts, monoisopropanolamine salts, diisopropanolamine salts and triisopropanolamine salts. Preferably, the salts may be alkali metal salts such as sodium salts. Specific examples of such alkali metal salts include monosodium uridylate and disodium uridylate, disodium uridylate being preferred from the standpoint of handleability.

The above active ingredients may be used alone or in combination of two or more.

There is no particular limitation on the origins of the active ingredients, and those derived from natural products such as yeast, bacteria, seafood, animals, and plants are suitable.

The muscular atrophy inhibitor according to the present invention can be used for practical purposes as a composition for food and drink products, supplements, prepared milk powder, enteral nutritional supplements, healthy food and drink products (including Food for specified health uses and Food with function claims), additives for animal feed, and pharmaceutical products for humans or animals other than humans.

When the agent according to the present invention is provided as the food and drink product, health food and drink product or prepared milk powder, it can be made into a food or drink product having a muscular atrophy inhibiting function by adding the above active ingredients to the known food and drink product as appropriate. The food and drink products of interest include milk and dairy products, seasonings, beverages, confectioneries, breads, noodles, oils and fats, processed meat products, processed marine products, processed agricultural products, frozen foods, and instant foods.

The novel food and drink products that have the muscular atrophy inhibiting effect can be produced by mixing with materials for the food and drink products. The shape of the food and drink products of interest can be selected from various forms, such as tablets, granules, capsules, powders, solutions, syrups, emulsions, and pastes. In addition to the active ingredients according to the present invention, various excipients and seasoning ingredients that can be used as foods may be added as needed in the production of those food products.

The food and drink product as described above may be provided and sold as a food and drink product labeled with the health application for inhibiting muscular atrophy. The act of "labeling" includes all acts to make the above application known to users, and all expressions that may evoke or analogize the above application fall under the act of "labeling" in this invention, regardless of the purpose of the labeling, the content of the labeling, and the object or medium to be labeled.

It is preferable that the above "labeling" be made by means of expressions that enable users to directly recognize the above application. Specific examples include the act of assigning, delivering, displaying for the purpose of assignment or delivery, or importing of goods or packages of the goods in relation to the food and drink products, which describe the above application, or the act of displaying or distributing advertisement materials, price lists or transaction documents in relation to the goods, which describes the above application, and the act of providing information about these contents, which describes the above application, through electromagnetic means (e.g., through the internet).

It is preferable that the contents of the labeling are those approved by the government or the like (e.g., labeling that has been approved based on various systems established by the government and is performed in a manner based on such approval). It is also desirable to attach such labeling to packages, containers, catalogs, pamphlets, POP, and other promotional materials at the places of sales, and other documents.

When the muscular atrophy inhibitor according to the present invention is practically provided as a pharmaceutical, supplement, enteral nutritional product, and the like, the above active ingredient can be formulated alone or in combination with formulation aids or the like. The formulation may be orally or parenterally administered, and it is preferably orally or enterally administrated.

The formulations as described above can be tablets, granules, capsules, granules, dispersions, solutions, syrups, emulsions, and the like for oral administration, and injections, sprays, ointments, patches, and the like, for parenteral administration.

In addition to the active ingredients according to the present invention, other formulation aids such as excipients, binders, disintegrants, lubricants, taste masking agents, dissolution aids, suspending agents, coating agents, and the like, may be used in combination as appropriate according to each dosage form.

The amount of the above active ingredient in the muscular atrophy inhibitor according to the present invention may be appropriately selected from the range of 0.1 to 30% (w/w), depending on the purpose of use (prevention, health or symptom relief, etc.), age of the subject, method of administration or intake, dosage form, and the like.

The amount of administration or intake of the muscular atrophy inhibitor according to the present invention may be appropriately selected from the range of 1 mg to 800 g per a day, although it will vary depending on the subject's age, weight, the degree of muscular atrophy, the method of administration or intake, and the like.

EXAMPLES

The present invention will be more specifically described by Examples, but the present invention is not limited by these Examples.

(Example 1) Study for Atrophy Inhibiting Effect on Myotube Cells

To evaluate the effects of pyrimidine nucleotides or precursors thereof on atrophy inhibition of myotube cell, we examined the extent to which pyrimidine nucleotides or precursors thereof inhibited dexamethasone-induced muscle atrophy.

Example 1-1

Mouse myoblast cell line C2C12 cells (RIKEN BRC, RCB0987) were suspended in growth medium (Dulbecco's modified Eagle's Medium supplemented with 10% FBS, 100 units/ml of penicillin, 100 μg/ml of streptomycin), seeded in 24-well plates, and incubated in a 37° C., 5% C02 incubator until the cell density reached 70-90%.

The growth medium was removed, and exchanged to a differentiation induction medium (Dulbecco's modified Eagle's Medium supplemented with 2% adult bovine serum, 100 units/ml of penicillin, 100 μg/ml of streptomycin). The cells were cultured for 4 days while exchanging the medium once every 2 days and differentiated into myotube cells. The medium was removed and exchanged to the following four media.

(1) Differentiation induction medium containing neither dexamethasone nor disodium uridylate [Dex (−), UMP (−)];

(2) Differentiation induction medium containing 100 μM dexamethasone but no disodium uridylate [Dex (+), UMP (−)];

(3) Differentiation induction medium containing 100 μM dexamethasone and 2 mM disodium uridylate [Dex (+), 2 mM UMP]; and (4) Differentiation induction medium containing 100 μM dexamethasone and 5 mM disodium uridylate [Dex (+), 5 mM UMP].

After 24 hours, the medium was changed again. After 48 hours, five positions near the center of the wells were photographed at magnifications of 100. Using ImageJ image analysis software, the diameters of 10 myotube cells per a photograph were measured in the order from the myotube cell having the largest diameter, and an average of 50 cells was determined to be the diameter of the myotube cell in each well. For statistical analysis, Dunnett's multiple comparison test was performed using the control group (differentiation induction medium containing 100 μM dexamethasone but no uridylic acid) as a control. The threshold for statistical significance was set to 5%. Photographs of representative examples of the respective groups are shown in FIG. 1. A statistically processed graph for the myotube cell diameter for each group is also shown in FIG. 2.

Figure 2:
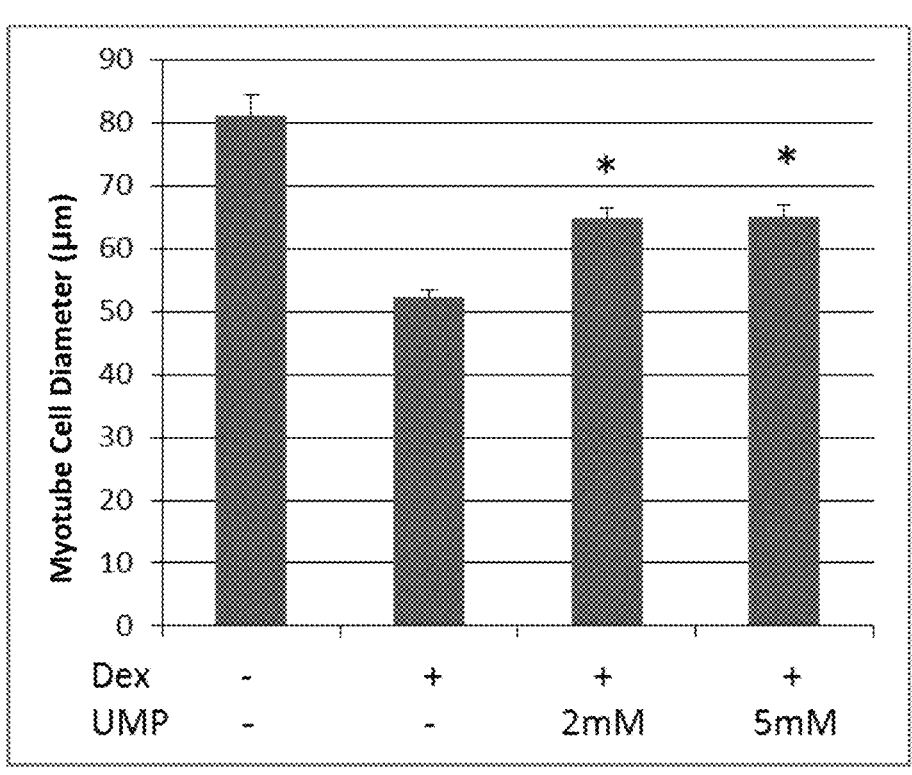
FIG. 2 shows an effect of uridylic acid on inhibition of dexamethasone-induced muscular atrophy in relation to a myotube cell diameter according to Example 1-1. In the figure, the Dex means dexamethasone, the UMP means disodium uridylate, the error bar means standard error, and the * means $p < 0.05$.

As shown in FIGS. 1 and 2, the myotube cell diameter was reduced by adding dexamethasone, but the reduction was suppressed for cells to which uridylic acid was added. These results indicate that uridylic acid has an excellent effect on atrophy inhibition of myotube cells.

Example 1-2

Mouse myoblast cell line C2C12 cells (RIKEN BRC, RCB0987) were suspended in growth medium (Dulbecco's modified Eagle's Medium supplemented with 10% FBS, 100 units/ml of penicillin, 100 μg/ml of streptomycin), seeded in 24-well plates, and incubated in a 37° C., 5% $CO_2$ incubator until the cell density reached 70-90%.

The growth medium was removed, and exchanged to a differentiation induction medium (Dulbecco's modified Eagle's Medium supplemented with 2% adult bovine serum, 100 units/ml of penicillin, 100 μg/ml of streptomycin). The cells were cultured for 4 days while exchanging the medium once every 2 days and differentiated into myotube cells. The medium was removed and exchanged to the following media:

(1) Differentiation induction medium containing no dexamethasone [Dex (−)];

(2) Differentiation induction medium containing 100 μM dexamethasone [Dex (+)];

(3) Differentiation induction medium containing 100 μM dexamethasone and a certain amount of disodium cytidylate [Dex (+), a certain amount of CMP];

(4) Differentiation induction medium containing 100 μM dexamethasone and a certain amount of cytidine [Dex (+), a certain amount of cytidine (which may be abbreviated as "Cyd")];

(5) Differentiation induction medium containing 100 μM dexamethasone and a certain amount of disodium uridylate [Dex (+), certain amount of UMP]; and (6) Differentiation induction medium containing 100 μM dexamethasone and a certain amount of uridine [Dex (+), certain amount of uridine].

After culturing the cells for 3 days, five positions near the center of the wells were photographed at magnifications of 100. Using ImageJ image analysis software, the diameters of 10 myotube cells per a photograph were measured in the order from the myotube cell having the largest diameter, and an average of 50 cells was determined to be the diameter of the myotube cell in each well. Statistical analysis was performed by t-test or Dunnett's multiple comparison test using the differentiation induction medium treatment group supplemented only with 100 μM dexamethasone as a control. The threshold for statistical significance was set to 5%. Photographs of representative examples of the respective groups are shown in FIG. 3.

Figure 3:
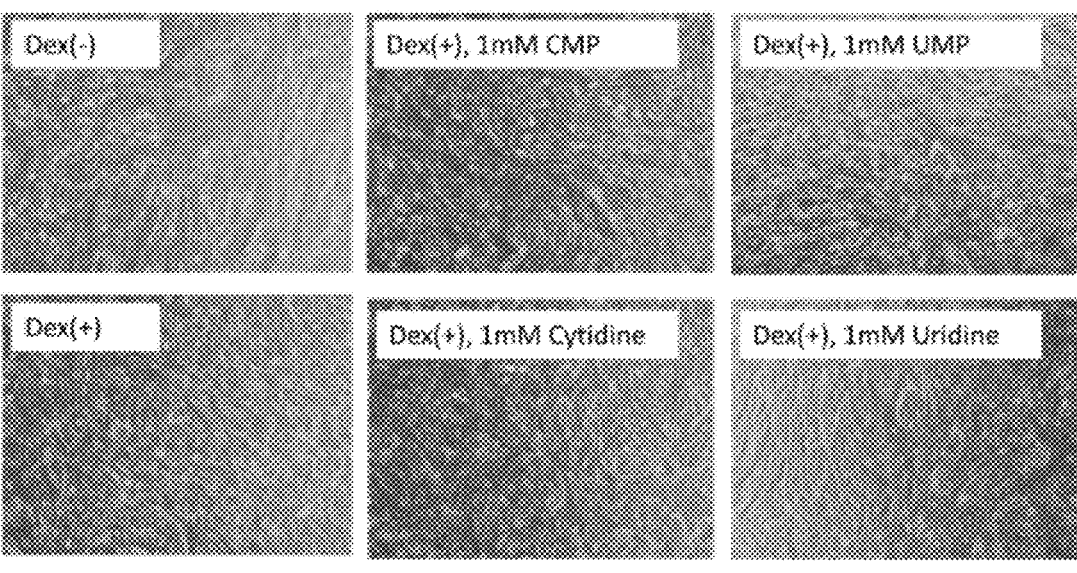
FIG. 3 shows effects of treatments with cytidylic acid, uridylic acid, cytidine, and uridine on inhibition of dexamethasone-induced muscular atrophy in C2C12 cells according to Example 1-2 by photographs at magnifications of 100. In the figure, the Dex (−) means non-treatment with dexamethasone, the Dex (+) means treatment with dexamethasone, the CMP means disodium cytidylate, and the UMP means disodium uridylate.

As shown in FIG. 3, the myotube cell diameter was reduced by the treatment with dexamethasone, while it was significantly increased by the treatments with cytidylic acid, uridylic acid, cytidine, and uridine.

Figure 4:
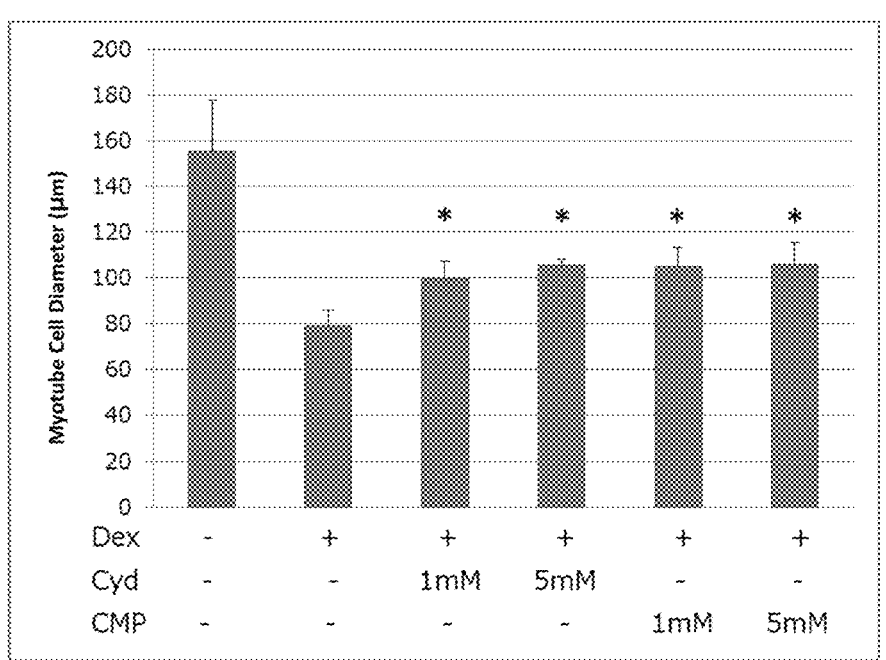
FIG. 4 shows effects of treatments with cytidylic acid and cytidine on inhibition of dexamethasone-induced muscular atrophy in C2C12 cells according to Examples 1-2. In the figure, the Dex means dexamethasone, the Cyd means cytidine, the CMP means disodium cytidylate, n=6, the error bar means standard error, and the * means $p < 0.05$.
Figure 5:
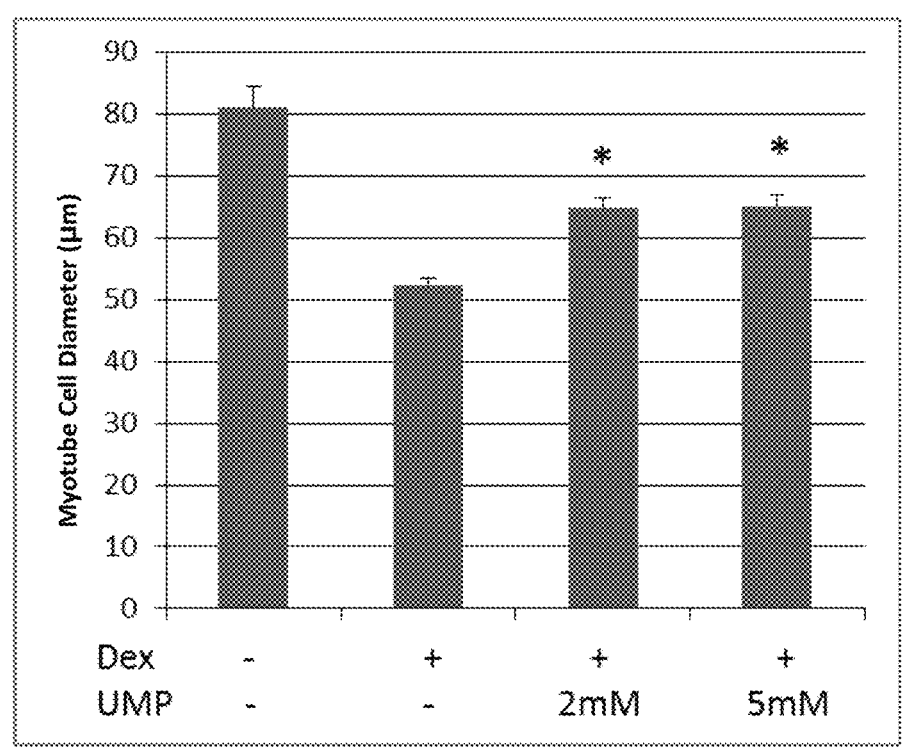
FIG. 5 shows an effect of a treatment with uridylic acid on inhibition of dexamethasone-induced muscular atrophy in C2C12 cells according to Example 1-2. In the figure, the Dex means dexamethasone, the UMP means disodium uridylate, n=6, error bar means standard error, and the * means means $p < 0.05$.
Figure 6:
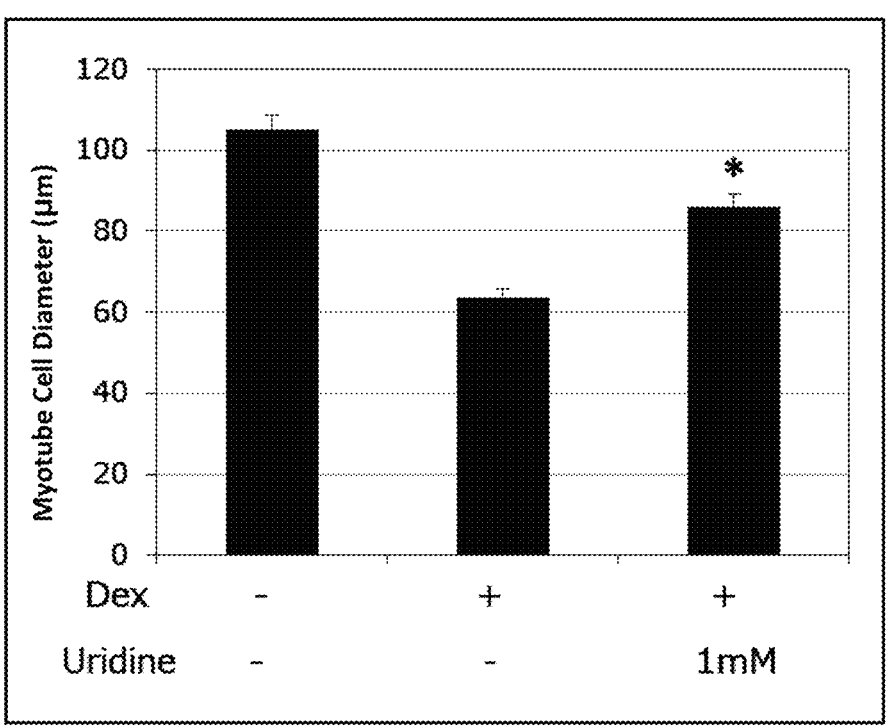
FIG. 6 shows an effect of a treatment with uridine on inhibition of dexamethasone-induced muscular atrophy in C2C12 cells according to Example 1-2. In the figure, the Dex means dexamethasone, n=6, error bar means standard error, and the * means $p < 0.05$.

Statistically processed graphs for the myotube cell diameter for each group are shown in FIGS. 4 to 6.

As shown in FIG. 4, the myotube cell diameter was reduced by the treatment with dexamethasone, while the myotube cell diameter was increased by the treatment with cytidylic acid and cytidine.

As shown in FIG. 5, the myotube cell diameter was reduced by the treatment with dexamethasone, while the myotube cell diameter was increased by the treatment with uridylic acid.

As shown in FIG. 6, the myotube cell diameter was reduced by the treatment with dexamethasone, while the myotube cell diameter was increased by the treatment with uridine.

These results indicate that cytidylic acid, uridylic acid, cytidine, and uridine have a myotube cell atrophy inhibiting effect.

(Example 2) Studies for Myotube Cell Atrophy Inhibiting Effect by Combination of Cytidylic Acid and Uridylic Acid In order to examine whether the combination of cytidylic acid and uridylic acid produces a stronger effect on atrophy inhibition of myotube cells, we evaluated the myotube cell atrophy inhibiting effect by the combination of cytidylic acid and uridylic acid by the same method as that of Example 1-2.

Figure 7:
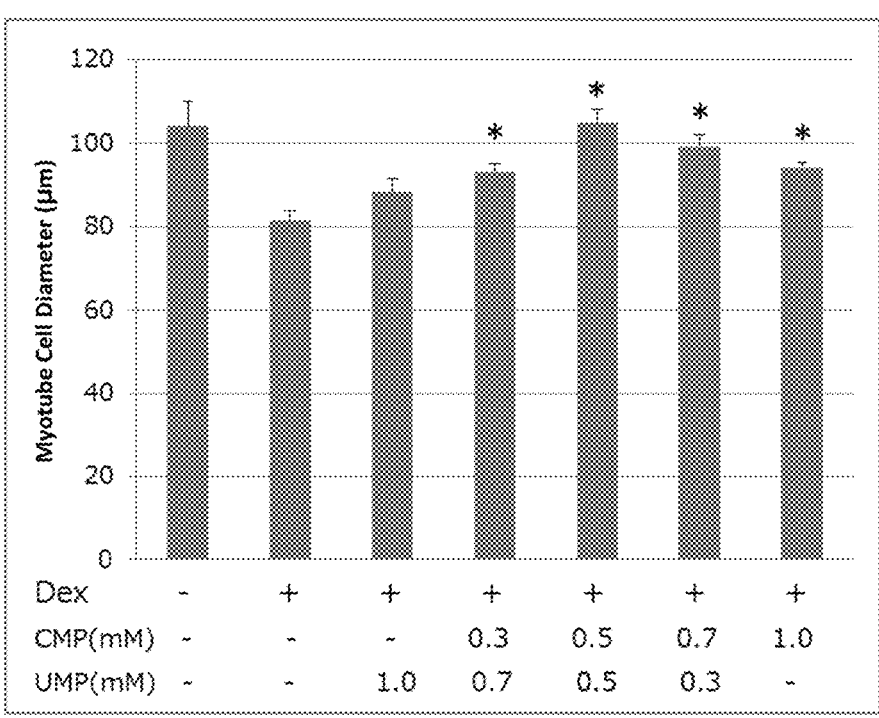
FIG. 7 shows effects of a combination of cytidylic acid and uridylic acid on inhibition of dexamethasone-induced muscular atrophy according to Example 2. In the figure, the Dex means dexamethasone, the CMP means disodium cytidylate, the UMP means disodium uridylate, n=6, error bar means standard error, and the * means $p < 0.05$.

Cytidylic acid and uridylic were added to the medium at the concentrations shown in FIG. 7 so that the total concentration of cytidylic acid and uridylic acid was 1000 μM. Otherwise, the same procedure as in Example 1-2 was used to evaluate the myotube cell atrophy inhibiting effect for the sample. The results are shown in FIG. 7.

As shown in FIG. 7, the myotube cell diameter was reduced by the treatment with dexamethasone, while the cell diameter was increased for both samples treated with cytidylic acid and uridylic acid. All of the samples that showed the muscular atrophy inhibiting effect, and in particular, the sample in which cytidylic acid was used in an amount equivalent to or more than that of uridylic acid showed the most remarkable muscular atrophy inhibiting effect.

(Example 3) Studies for Myotube Cell Atrophy Inhibiting Effect by Combination of Cytidylic Acid and Uridylic Acid and Combination of Cytidine and Uridine In order to examine whether the combination of cytidylic acid and uridylic acid produces a stronger effect on atrophy inhibition of myotube cells, we evaluated the myotube cell atrophy inhibiting effect by the combination of cytidylic acid and uridylic acid by the same method as that of Example 1-2.

In Example 2, the total concentration of cytidylic acid/uridylic acid added to the medium was adjusted to 1000 μM and a ratio of the cytidylic acid/uridylic acid was varied. In Example 3, the myotube cell atrophy inhibiting effect was evaluated when the total concentration was 2000 μM; 1 mM (1000 μM) of cytidylic acid+1 mM (1000 μM) of uridylic acid.

Similarly, the effect of the combination of cytidine and uridine were also evaluated. These results are shown in FIG. 8.

Figure 8:
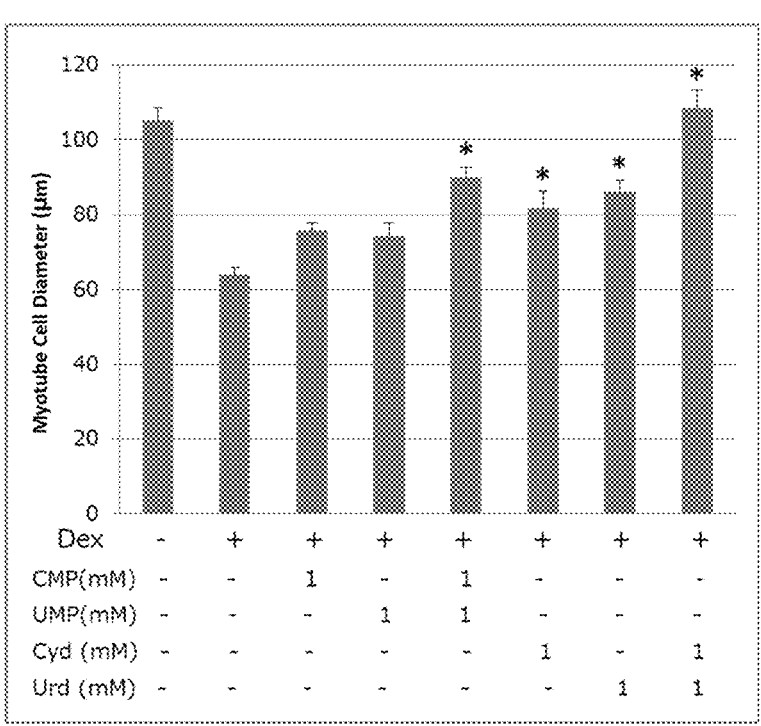
FIG. 8 shows effects of a combination of cytidylic acid and uridylic acid and a combination of cytidine and uridine on inhibition of dexamethasone-induced muscular atrophy according to Example 3. In the figure, the Dex means dexamethasone, the CMP means disodium cytidylate, the UMP means disodium uridylate, the Cyd means cytidine, the Urd means uridine, n=6, the error bar means standard error, and the * means $p < 0.05$, and 1 mM CMP+UMP means that 1 mM cytidylic acid+1 mM uridylic acid, 2 mM in total, were added; and 1 mM Cyd+Urd means that 1 mM cytidine+1 mM uridine, 2 mM in total, were added.

As shown in FIG. 8, the myotube cell diameter was reduced by the treatment with dexamethasone, while it was significantly increased by the treatments with cytidylic acid, uridylic acid, cytidine, and uridine. Further, the combination of cytidylic acid and uridylic acid and the combination of cytidine and uridine significantly increased the myotube cell diameter.

These results indicate that the combination of cytidylic acid and uridylic acid, as well as the combination of cytidine and uridine, produces an additive effect on atrophy inhibition of myotube cells.

(Example 4) Expression Inhibiting Effect on Muscular Atrophy-Related Genes (Atrogin-1 and MuRF1)

Mouse myoblast cell line C2C12 cells were suspended in growth medium, seeded in 24-well plates, and incubated in a 37° C., 5% C02 incubator until the cell density reached 70-90%. The growth medium was removed, and exchanged to a differentiation induction medium. The cells were cultured for 6 days while exchanging the medium once every 2 days and differentiated into myotube cells. The medium was removed and exchanged to a differentiation induction medium or a differentiation induction medium containing a test substance. After 48 hours, the medium was removed and replaced with a differentiation induction medium, a differentiation induction medium supplemented only with 1 µM dexamethasone, or a medium supplemented with 1 µM dexamethasone and test substances (a certain amount of UMP (disodium uridylate), a certain amount of Urd (uridine), and a certain amount of UMP (disodium uridylate)).

After 24 hours, the medium was removed and total RNA was extracted from the cells using RNeasy Mini kit (QIAGEN) or NucleoSpin RNA (Takara Bio).

Using the total RNA as a template, a reverse transcription reaction solution was prepared using the ReverTra Ace(R) qPCR RT Kit (Toyobo). The reverse transcription reaction solution, GoTaq(R) qPCR Master Mix (Promega), and a real-time PCR device, Thermal Cycler Dice Real Time System (Takara Bio), were used to measure mRNA expression levels of Atrogin-1, MuRF1 and β-actin as an internal standard. Analysis was performed by relative quantification, and mRNA expression levels were corrected using the β-actin mRNA expression level as an endogenous control. For statistical analysis, Dunnett's multiple comparison test was performed using the differentiation induction medium-treated group supplemented with only 100 µM dexamethasone as a control. The threshold for statistical significance was set to 5%. The results are shown in FIGS. 9 to 12.

Figure 9:
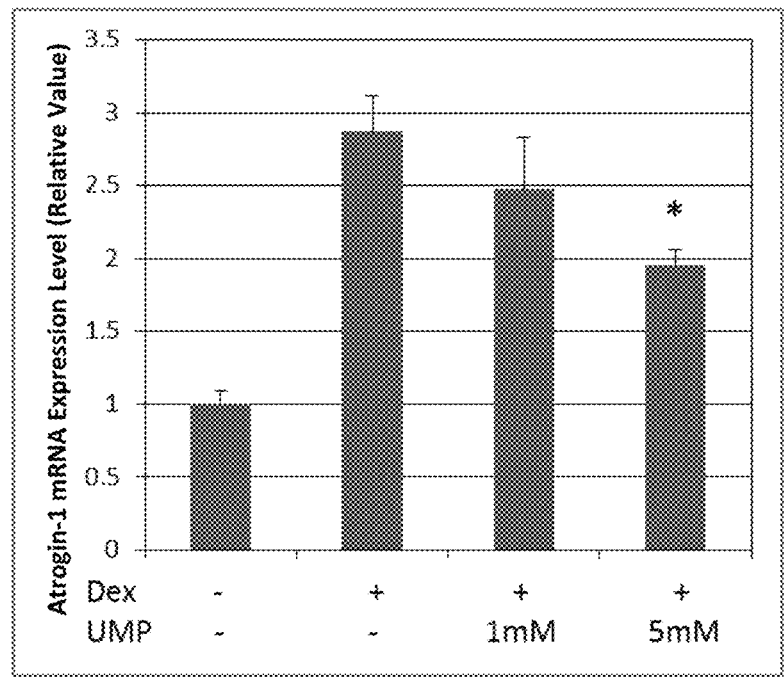
FIG. 9 shows an effect of uridylic acid on inhibition of Atrogin-1 gene expression according to Example 4. In the figure, the Dex means dexamethasone, the UMP means disodium uridylate, n=6, the error bars means standard error, and the * means $p < 0.05$.

As shown in FIG. 9, the treatment with dexamethasone increased the mRNA expression level of Atrogin-1, while the treatment with uridylic acid decreased the mRNA expression level of Atrogin-1.

Figure 10:
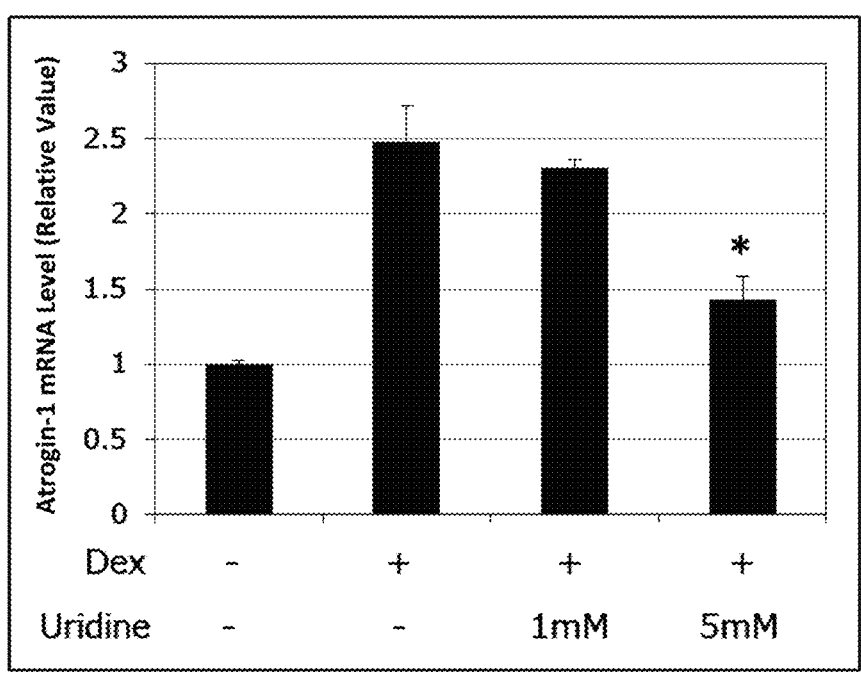
FIG. 10 shows an effect of uridine on inhibition of Atrogin-1 gene expression according to Example 4. In the figure, the Dex means dexamethasone, n=6, the error bar means standard error, and the * means $p < 0.05$.

As shown in FIG. 10, the treatment with dexamethasone increased the mRNA expression level of Atrogin-1, while the treatment with uridine decreased the mRNA expression level of Atrogin-1.

Figure 11:
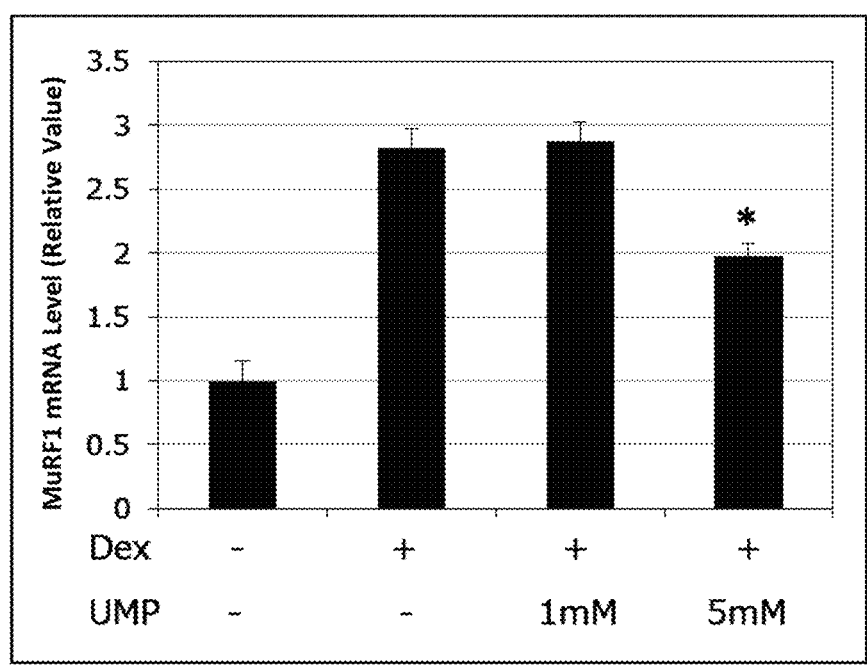
FIG. 11 shows an effect of uridylic acid on inhibition of MuRF1 gene expression according to Example 4. In the figure, the Dex means dexamethasone, the UMP means disodium uridylate, n=6, the error bar means standard error, and the * means p<0.05.

As shown in FIG. 11, the treatment with dexamethasone increased the mRNA expression level of MuRF1, while the treatment with uridylic acid decreased the mRNA expression level of MuRF1.

Figure 12:
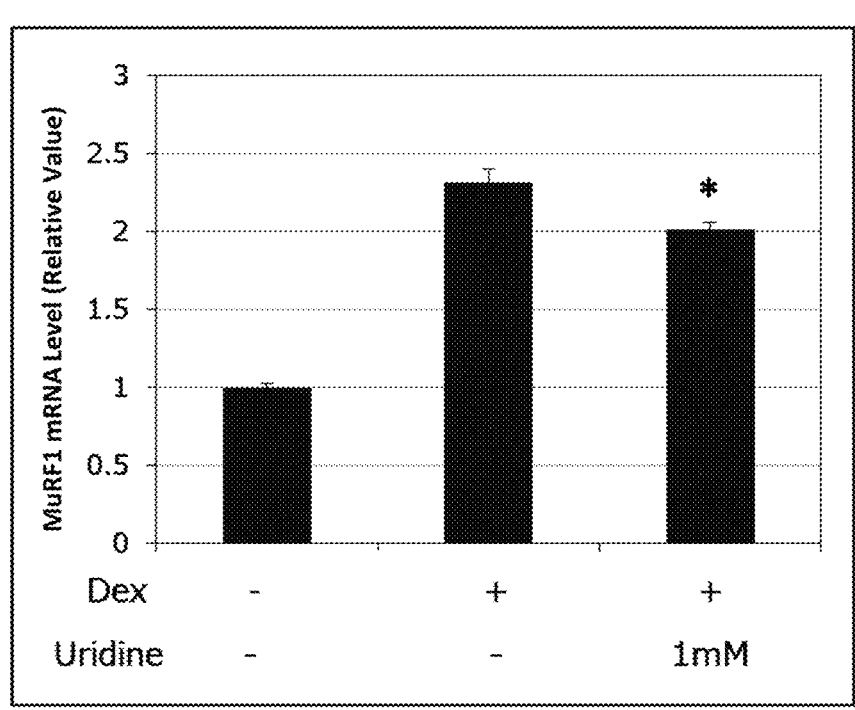
FIG. 12 shows an effect of uridine on inhibition of MuRF1 gene expression according to Example 4. In the figure, the Dex means dexamethasone, n=6, error bar means standard error, and the * means p<0.05.

As shown in FIG. 12, the treatment with dexamethasone increased the mRNA expression level of MuRF1, while the treatment with uridine decreased the mRNA expression level of MuRF1.

These results indicate that uridylic acid and uridine have an excellent inhibiting effect on the expression of muscular atrophy-related genes (Atrogin-1 and MuRF1).

The inhibiting effect on the expression of muscular atrophy-related genes shown in the Examples may not necessarily explain the entire mechanism of action of the inhibiting effect on muscular atrophy according to the present invention. The fact that an additive effect is achieved by the combination of cytidylic acid and uridylic acid, as described in Example 3, suggests that the inhibiting effect on muscular atrophy according to the present invention may not be due to a single mechanism of action, but may be due to multiple mechanisms of action.

The invention claimed is:

1. A method for inhibiting muscular atrophy in an individual in need thereof, wherein the method comprises;
    (a) providing a formulation or a pharmaceutical comprising:
    (i) cytidine or a cytidylic acid salt;
    (ii) uridine or uridylic acid salt;
    (iii) cytidine and uridine; or
    (iv) cytidylic acid or a cytidylic acid salt, and uridylic acid or a uridylic acid salt; and
    (b) administrating to the individual in need thereof the formulation or pharmaceutical of (a).

2. The method for inhibiting muscular atrophy according to claim 1, wherein the formulation or pharmaceutical is formulated for enteral or parenteral administration, and the formulation is enterally or parenterally administered.

3. The method according to claim 1, wherein the formulation or pharmaceutical is formulated for oral administration and is orally administered.

4. The method according to claim 1, wherein the oral formulation or pharmaceutical is formulated as a tablet, a granule, a capsule, a dispersions, a solution, a syrup, an emulsion, an injection, a supplement or a spray.

5. The method of claim 1, wherein the formulation or pharmaceutical is formulated for injection, or for administration as a spray, ointment or patch, and is administered by injection, or by spraying, or use application as an ointment, paste or patch.

6. The method of claim 1, wherein the formulation or pharmaceutical further comprises: an excipient, a binder, a disintegrant, a lubricant, a taste masking agent, a dissolution aid, a suspending agent, a coating agent or any combination thereof.

7. The method of claim 1, wherein the cytidine and uridine, or cytidylic acid and uridylic acid, are formulated as a daily dosage of between about 1 mg to 800 gram per day.

8. The method of claim 1, wherein the formulation or pharmaceutical is formulated or mixed with a food or a drink product before administration to the individual in need thereof.

9. The method of claim 8, wherein the food or drink product is or comprises: a milk or a dairy product, a seasoning, a beverage, a confectionery, a bread, a noodle, an oils or a fat, a processed meat product, a processed marine product, a processed agricultural product, a frozen food or an instant food.

10. The method of claim 9, wherein the milk or dairy product is or comprises a milk powder.

11. The method of claim 1, wherein the cytidylic acid comprises:
    (a) an alkali metal salt, optionally a sodium or a potassium salt;
    (b) an alkaline earth metal salts, optionally a calcium, magnesium or barium salt;
    (c) a basic amino acid salt, optionally an arginine or a lysine salt;
    (d) an ammonium salt, optionally an ammonium or a tricyclohexylammonium salt;
    (e) an alkanolamine salt, optionally a monoethanolamine salt, a diethanolamine salt or a triethanolamine salt, (f) a monoisopropanolamine salt, a diisopropanolamine salt or a triisopropanolamine salt; or (b) any combination of (a) to (e).

12. The method of claim 11, wherein the cytidylic acid comprises a monosodium cytidylate or a disodium cytidylate.

13. The method of claim 1, wherein the uridylic acid comprises:

(a) an alkali metal salt, optionally a sodium or a potassium salt;

(b) an alkaline earth metal salts, optionally a calcium, magnesium or barium salt;

(c) a basic amino acid salt, optionally an arginine or a lysine salt;

(d) an ammonium salt, optionally an ammonium or a tricyclohexylammonium salt;

(e) an alkanolamine salt, optionally a monoethanolamine salt, a diethanolamine salt or a triethanolamine salt, (f) a monoisopropanolamine salt, a diisopropanolamine salt or a triisopropanolamine salt; or (g) any combination of (a) to (e).

14. The method of claim 13, wherein the uridylic acid comprises a monosodium uridylic or a disodium uridylic.

15. The method of claim 13, wherein the muscular atrophy inhibited comprises skeletal muscle atrophy.

16. A method for inhibiting a ubiquitin-proteasome proteolytic system in an individual in need thereof, wherein the method comprises:

(a) providing a formulation or pharmaceutical comprising:

(i) cytidine or a cytidylic acid salt;

(ii) uridine or uridylic acid salt;

(iii) cytidine and uridine; or (iv) cytidylic acid or a cytidylic acid salt, and uridylic acid or a uridylic acid salt; and (b) administrating to the individual in need thereof the formulation or pharmaceutical of (a).

17. A method for inhibiting expression of an Atrogin-1 gene in an individual in need thereof, wherein the method comprises:

(a) providing a formulation or pharmaceutical comprising:

(i) cytidine or a cytidylic acid salt;

(ii) uridine or uridylic acid salt;

(iii) cytidine and uridine; or (iv) cytidylic acid or a cytidylic acid salt, and uridylic acid or a uridylic acid salt; and (b) administrating to the individual in need thereof the formulation or pharmaceutical of (a).

18. The method of claim 1, wherein active ingredients in the formulation or pharmaceutical consist of cytidine or a cytidylic acid salt.

19. The method of claim 1, wherein active ingredients in the formulation or pharmaceutical consist of uridine or uridylic acid salt.

20. The method of claim 1, wherein active ingredients in the formulation or pharmaceutical consist of cytidine and uridine.

21. The method of claim 1, wherein active ingredients in the formulation or pharmaceutical consist of cytidylic acid or a cytidylic acid salt, and uridylic acid or a uridylic acid salt.

\* \* \* \* \*